(12) United States Patent
Hamano (10) Patent No.: US 8,240,303 B2
(45) Date of Patent: Aug. 14, 2012

(54) LIQUID EJECTION DEVICE

(75) Inventor: Soji Hamano, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 9 days.

(21) Appl. No.: 12/834,622

(22) Filed: Jul. 12, 2010

(65) Prior Publication Data

US 2010/0275914 A1 Nov. 4, 2010

Related U.S. Application Data

(62) Division of application No. 11/694,139, filed on Mar. 30, 2007, now Pat. No. 7,779,835.

(30) Foreign Application Priority Data

Apr. 17, 2006 (JP) .................................. 2006-113703

(51) Int. Cl.
*A61M 11/00* (2006.01)
(52) U.S. Cl. ............................... 128/203.12; 128/200.23
(58) Field of Classification Search ............. 128/200.14, 128/205.23, 200.23, 200.24, 203.24, 203.12, 128/200.17, 203.15
See application file for complete search history.

(56) References Cited

U.S. PATENT DOCUMENTS

| | | | | |
|---|---|---|---|---|
| 5,284,133 A | 2/1994 | Burns et al. | ............... | 128/200.23 |
| 5,363,842 A | 11/1994 | Mishelevich et al. | .... | 128/200.14 |
| 5,497,764 A | 3/1996 | Ritson et al. | ............. | 128/200.14 |
| 5,692,492 A | 12/1997 | Bruna et al. | ............. | 128/200.23 |
| 6,081,284 A | 6/2000 | Tosaka et al. | .................. | 347/87 |
| 2008/0011292 A1 | 1/2008 | Sugita et al. | ............. | 128/200.19 |
| 2008/0022998 A1 | 1/2008 | Hamano et al. | .......... | 128/200.14 |

FOREIGN PATENT DOCUMENTS

| | | |
|---|---|---|
| EP | 1 618 803 | 1/2006 |
| GB | 2 406 283 | 3/2005 |
| JP | 7-314718 | 12/1995 |
| JP | 8-506746 | 7/1996 |
| JP | 2000-157634 | 6/2000 |
| JP | 2003-305862 | 10/2003 |
| JP | 2004-97617 | 4/2004 |
| JP | 2006-003438 | 1/2006 |
| WO | WO 02/04043 A2 | 1/2002 |

OTHER PUBLICATIONS

European Search Report dated Aug. 20, 2007, for corresponding Appln. No. 07105537.0-2310.

*Primary Examiner* — Steven Douglas
(74) *Attorney, Agent, or Firm* — Fitzpatrick, Cella, Harper & Scinto (57) ABSTRACT

A liquid ejection device of the present invention includes an inhaling port portion, an ejection head for ejecting a liquid to be inhaled by a user through the inhaling port portion, a first sensor for detecting an action of the user relating to inhalation, a second sensor for detecting another action of the user relating to inhalation, the second sensor being different from the first sensor, and a determining portion for determining an operation of ejecting the liquid of the ejection head in response to both a first signal output from the first sensor and a second signal output from the second sensor, wherein the determining portion enables ejection of the liquid from the ejection head when both the first signal and the second signal are signals indicating inhalation intention of the user.

7 Claims, 7 Drawing Sheets

LIQUID EJECTION DEVICE

RELATED APPLICATIONS

The present application is a divisional of Ser. No. 11/694,139, filed Mar. 30, 2007, now U.S. Pat. No. 7,779,835, claims benefit of that application under 35 U.S.C. §120, and claims priority benefit under 35 U.S.C. §119 of Japanese Patent Application 2006-113703, filed Apr. 17, 2006; the entire contents of each of the two mentioned prior applications are incorporated herein by reference.

BACKGROUND OF THE INVENTION

1. Field of the Invention

The present invention relates to a liquid ejection device such as a drug ejection device which ejects a drug to be inhaled through a respiratory system of a human body. The present invention particularly relates to a technology of allowing a user to inhale an ejected liquid more reliably in a liquid ejection device for health care adapted so as to be portably owned by the user.

2. Description of the Related Art

In recent years, owing to development in medicine and science, the average life span has become long and we are entering an aging society. On the other hand, change in eating habits and living environment, and environmental pollution are accelerated. New diseases and infection diseases by viruses and germs have been found. Therefore, people feel increased anxiety about health. Especially in the countries called developed countries, an increase in the number of patients of the diseases caused by lifestyle habits such as diabetes and hypertension has become the problem.

Meanwhile, the number of medical institutions does not increase to such an extent as to cope with such increase in the number of patients, and some areas have no medical institution available for ambulant patients. Therefore, the future countermeasure including policies has become a matter of concern.

Describing with a concrete example, of the patients of diabetes on the increase at present, the patients of insulin-dependent diabetes mellitus called I type do not have insulin secreted from their pancreas. Therefore, they need to be regularly given insulin. Administration of insulin is performed by hypodermic injection at present, and therefore, it gives a large physical and mental burden on the users.

In order to reduce such a burden on the users, a pen type injector which has a fine needle and gives less pain has been developed. However, since the patients of I type diabetes live in the same manner as normal healthy people except that they needs to have regular administration of insulin, they are mentally reluctant to have injection in public even with a pen type injector. Therefore, administration at a proper time is difficult.

As a result, such a method brings about the possibility that proper treatment for the users is not performed. However, by a drug ejection device which allows the users to take a drug by inhalation, treatment for the users who can utilize an information database such as electronic medical records is being materialized. Such a drug ejection device has a storage unit which stores information relating to the individual users including the medical records and the information of the prescription of the users. The drug ejection device also has an ejection control unit which is a portable terminal also having the function of the inhalator device that ejects a drug as minute droplets to be inhaled by a user, and also controls the inhalator device according to an air intake profile to allow the inhalator to eject the drug so that the user can inhale the drug according to the information of the prescription.

Such a drug ejection device can accurately manage the dosage and administration interval of the drug according to the prescription, and conducts proper ejection control according to the air intake profile of the individual users. Therefore, the drug ejection device can efficiently give the drug. According to this, the medical appliance such as an injector does not need to be used on the occasion of administration of a drug as in the conventional method. Therefore, it is known that not only the operation can be easily made without expert knowledge, but also pain to the users caused by injection needles can be eliminated (see WO 1995/001137, WO 2002/004043).

On one hand, about the reliability and proper operation of the drug ejection device, a burden is likely to be imposed on the users. For example, when the user suffers a chronic disease and needs to be given a drug regularly, administration and management of the drug are left to the reliability of the drug ejection device and proper operation of the user. In such a case, the function of allowing the user to recognize the malfunction of the device including a drug ejection unit, physical mounting mistake of consumables and the like in some manner is preferably included.

Even when the drug ejection unit in the drug ejection device is set normally, the ejected liquid needs to be reliably inhaled by the user.

In order to allow the user to reliably inhale the liquid ejected to the user through the oral cavity or the nasal cavity, the method of taking the inspiration air of the user as negative pressure (air pressure lower than atmospheric pressure) in the inhaling passage, and actuating ejection with the timing of the inspiration as the reference is considered as general ejection actuation method. Namely, when the negative pressure in the inhaling passage exceeds a predetermined value, the drug ejection device determines that the user performs inhalation and starts ejection. However, a portable drug ejection device or the like takes the atmospheric pressure change due to a gust as occurrence of the negative pressure when the gust occurs outdoors, and the ejection actuation unit is likely to operate and eject a liquid at the undesired time. In the ejection device which takes the inhalation intention of the user by the user simply pressing an actuation button or the like, and ejects a liquid, an actuation button or the like can be erroneously pressed to eject a liquid at an undesired time.

SUMMARY OF THE INVENTION

In view of the above problems, a liquid ejection device of the present invention for ejecting a liquid to be inhaled by a user through an inhaling port portion includes: a first sensor for detecting an action of the user relating to inhalation; a second sensor for detecting another action of the user relating to inhalation, the second sensor for different from the first sensor; and a determining portion for determining an operation of ejecting the liquid of the ejection head in response to both a first signal output from the first sensor and a second signal output from the second sensor, wherein the determining portion enables ejection of the liquid from the ejection head when both the first signal and the second signal are signals indicating inhalation intention of the user.

According to the present invention, by providing two or more sensors for detecting the operation of the user relating to inhalation, the inhalation intention of the user can be more reliably confirmed. As a result, the ejected liquid can be more reliably inhaled by the user. For example, only when detecting that a portion of the body of the user contacts the inhaling port portion and detecting the inhaling air flow by a pressure sensor or the like, the liquid ejection device starts ejection. Thereby, the trouble of detecting the negative pressure occurring independently of inhalation and ejecting a liquid can be prevented or reduced.

Other features and advantages of the present invention will be apparent from the following description taken in conjunction with the accompanying drawings, in which like reference characters designate the same or similar portions throughout the figures thereof.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

An embodiment of a liquid ejection device of the present invention which allows a user to inhale a liquid through at least one of an oral cavity and a nasal cavity will be described.

An embodiment of the liquid ejection device of the present invention has an inhaling port portion, an ejection head ejecting a liquid to be inhaled by a user through the inhaling port portion, a first sensor detecting an action of the user relating to inhalation, a second sensor differing from the first sensor and detecting another action of the user relating to inhalation, and a determining portion determining an operation of ejecting the liquid of the ejection head in response to both a first signal output from the first sensor and a second signal output from the second sensor.

The determining portion enables ejection of the liquid from the ejection head when both the first signal and the second signal are signals indicating inhalation intention of the user.

In this case, the inhaling port portion is provided at one end portion of the passage for introducing ejection liquid into at least one of the oral cavity and the nasal cavity of the user.

In another embodiment of the present invention, a third sensor differing from any of the first sensor and the second sensor, and detecting still another action of the user relating to inhalation may be included. The determining portion enables ejection of the liquid from the ejection head when all of the first signal, the second signal and a third signal output from the third sensor are signals indicating the inhalation intention of the user. Thereby, the determining portion can confirm that the user starts inhalation action more reliably, and allows the user to inhale the ejection liquid more reliably.

As the sensors, the following sensors are cited.

First, a pressure sensor or a flowmeter that is provided in an inhaling passage is cited. The inhaling passage is the place where the liquid is ejected as droplets and extends from the air intake port to the inhaling port portion. Each of such sensors outputs a signal indicating the inhalation intention of the user by detecting a predetermined negative pressure or flow rate. Namely, by a predetermined negative pressure or flow rate being detected, the sensor determines that inhalation of the user is performed.

Second, a contact detection sensor provided in the inhaling port portion is cited. The contact detection sensor outputs a signal indicating the inhalation intention of the user by detecting a contact state of the user with the inhaling port portion.

Third, a hold detection sensor provided in a liquid ejection device body is cited. The hold detection sensor outputs a signal indicating the inhalation intention of the user by a detecting hold state of the user on the liquid ejection device body.

An exemplary embodiment is the embodiment having a pressure sensor or a flowmeter as the first sensor, having the contact detection sensor provided in the inhaling port portion as the second sensor, and having the hold detection sensor provided in the liquid ejection device body as the third sensor. The determining portion enables ejection of the liquid from the ejection head only when obtaining the signals indicating the inhalation intention of the user by all of the three sensors.

The liquid is typically a drug solution, but may be other liquid. As the sensor, only a push button simply provided for allowing the user to press it on the occasion of inhalation may be adopted. By detecting that the push button is pressed, the sensor determines the inhalation intention of the user and transmits a signal to the determining portion.

In the present invention, in order to confirm in advance whether ejection of the liquid is reliably performed or not, preliminary ejection which is not inhaled can be performed before ejection by inhalation. On this occasion, the determining portion drives the ejection head so as to eject the liquid from the ejection head in response to a signal to start preliminary ejection regardless of the presence or absence of the signal indicating the inhalation intention of the user by the sensor. In addition to the above described configuration, the liquid ejection device may further have a mounting portion for attachably and detachably mounting a head tank unit, and a mounting detection portion for detecting that the head tank unit is mounted to the mounting portion.

In this case, the head tank unit is the unit which is a combination of an ejection head portion, a tank portion storing a liquid and a liquid communication passage from the tank portion to the head portion. The determining portion enables ejection of the liquid from the ejection head when the mounting detection portion outputs a signal indicating mounting of the head tank unit to the mounting portion in addition to the signal indicating the inhalation intention of the user by the sensor.

According to this, by enabling ejection when detecting that the head tank unit is in the mounted state, the user can inhale a liquid more reliably.

Further, in the present invention, the determining portion starts ejection of the liquid from the ejection head when all the sensors output the signals indicating the inhalation intention of the user, and after a predetermined time elapses from the start, the determining portion can stop ejection of the liquid from the ejection head regardless of the output signals. Namely, while all the sensors output the signals indicating the inhalation intention of the user, the liquid ejection device of the present invention is in the state in which the liquid can be ejected, but after it ejects a predetermined ejection amount, the liquid ejection device can automatically stop ejection. Thereby, the user can reliably inhale a desired amount of liquid.

In addition to the above described configuration, the preparatory unit preparing the head tank unit in the state capable of ejection may be further included. When the head tank unit is brought into the preparation completed state by the preparatory unit, ejection operation can be started. According to this, at the time of preparation completed state in which the head tank unit is prepared to be capable of ejecting by the preparatory unit, ejection is enabled, and thereby, the user can inhale the liquid more reliably.

In the above described configuration, on the occasion of the determining portion enabling ejection, ejection enabling is made effective only for a predetermined time. This is because if ejection is enabled for more than the required time, there is the fear that when the user returns from the inhaling posture and assumes another posture, the liquid is ejected, and start of undesired liquid ejection operation is carried out. It should be noted that the predetermined time shall be the time sufficiently longer than the time required for one inhalation.

As one embodiment of the present invention, a liquid ejection device used as a drug inhaling device will be described as an example.

Figure 1:
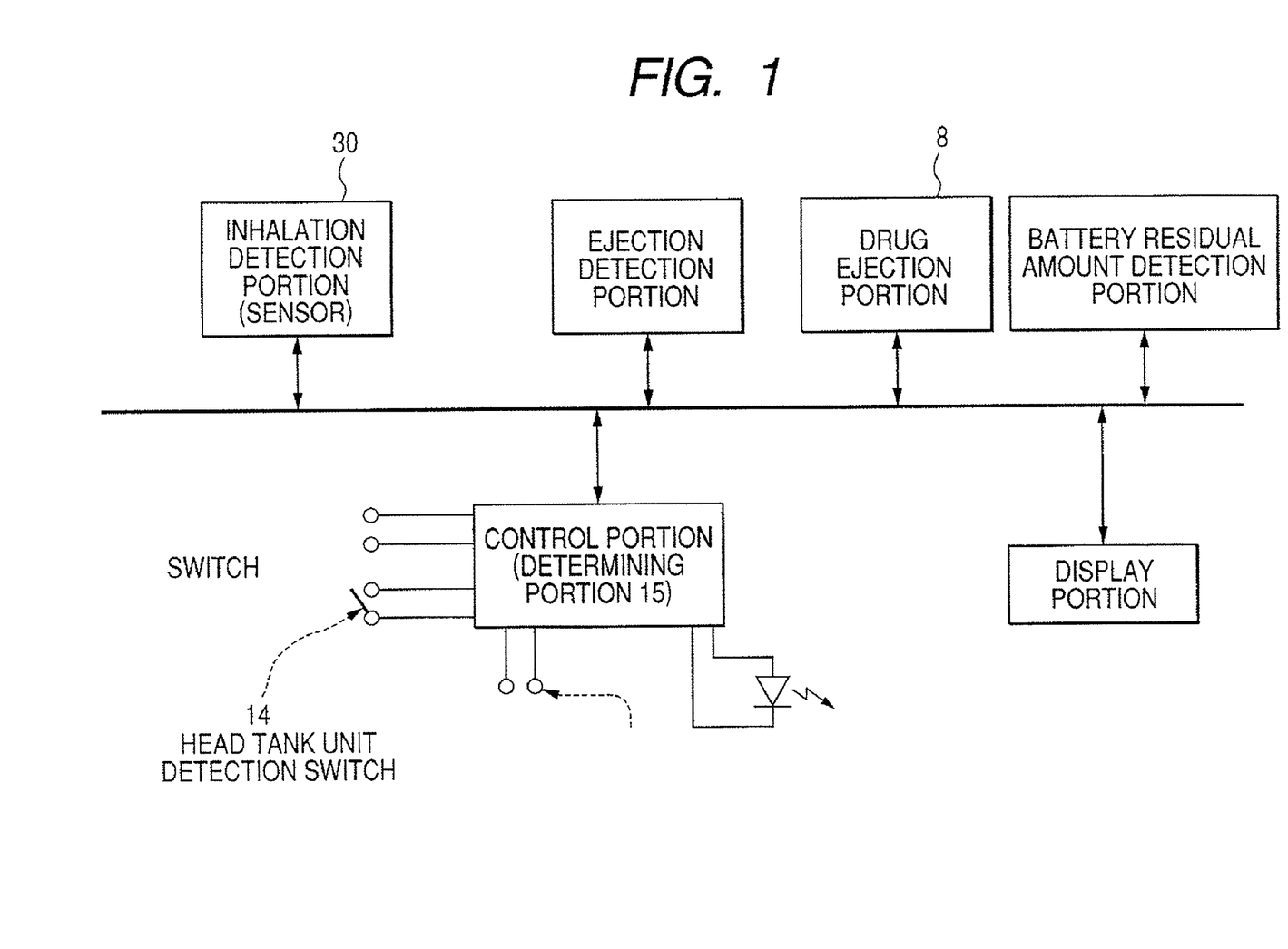
FIG. 1 is a schematic diagram illustrating an electrical internal configuration of an inhaling device according to an embodiment of the present invention.

FIG. 1 is a block diagram showing an electrical internal configuration of an inhaling device 1 according to the embodiment. A control unit controlling the entire inhaling device is disposed on a control board of the inhaling device, and a determining portion 15 enabling ejection of a liquid in the present invention is included in a portion of the control unit. The control unit receives signals from an inhalation detection unit 30 (pressure sensor) detecting the inhalation air flow of a user, an ejection detection unit for detecting ejection of a drug, a drug ejection unit (head tank unit) ejecting the drug, a detection unit detecting the residual amount of a battery and the like. The control unit is connected to various kinds of switches used in the present invention such as an ejection unit detection switch 14.

Figure 2:
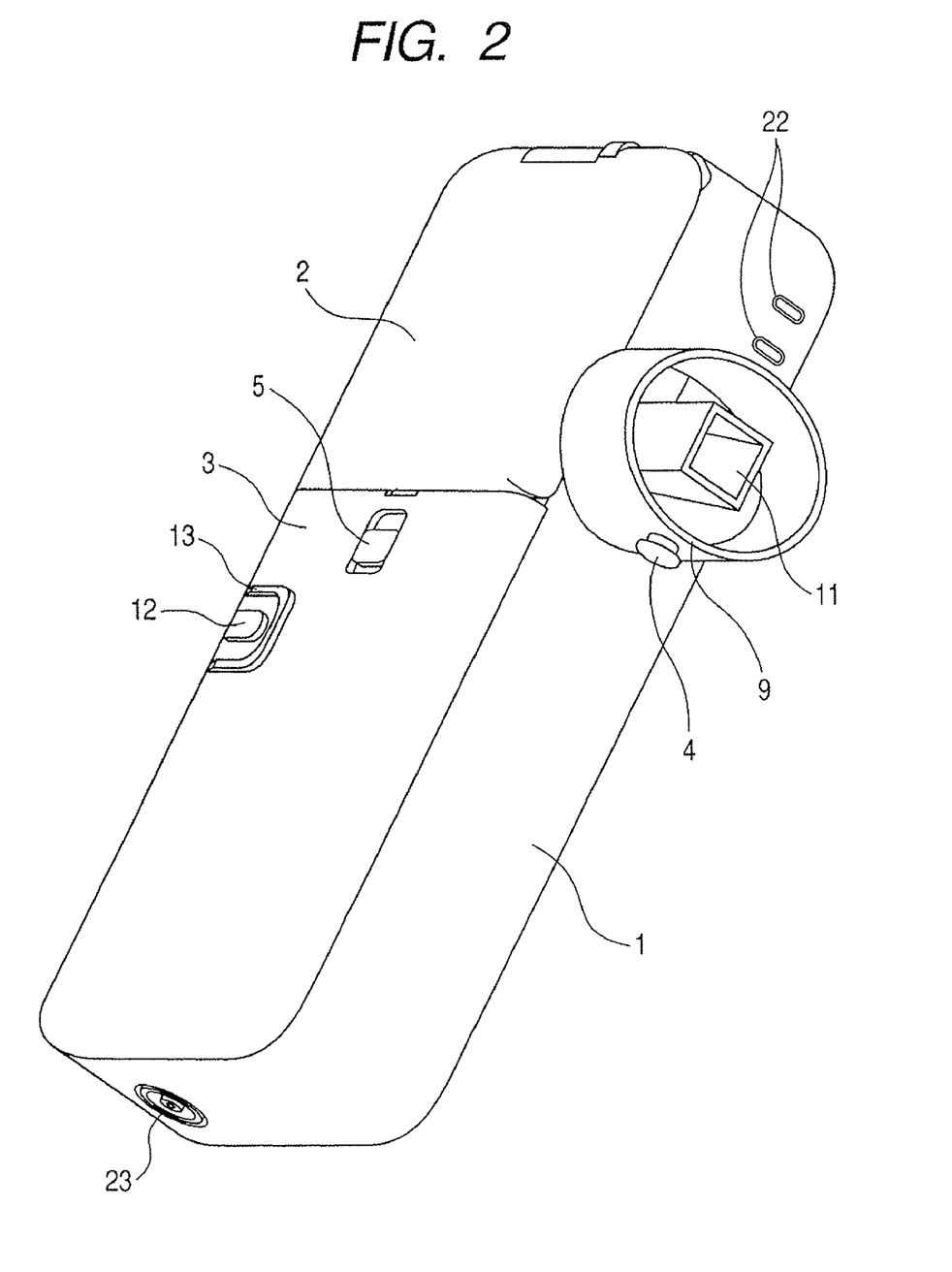
FIG. 2 is a view showing the appearance of the inhaling device according to an embodiment of the present invention.
Figure 3:
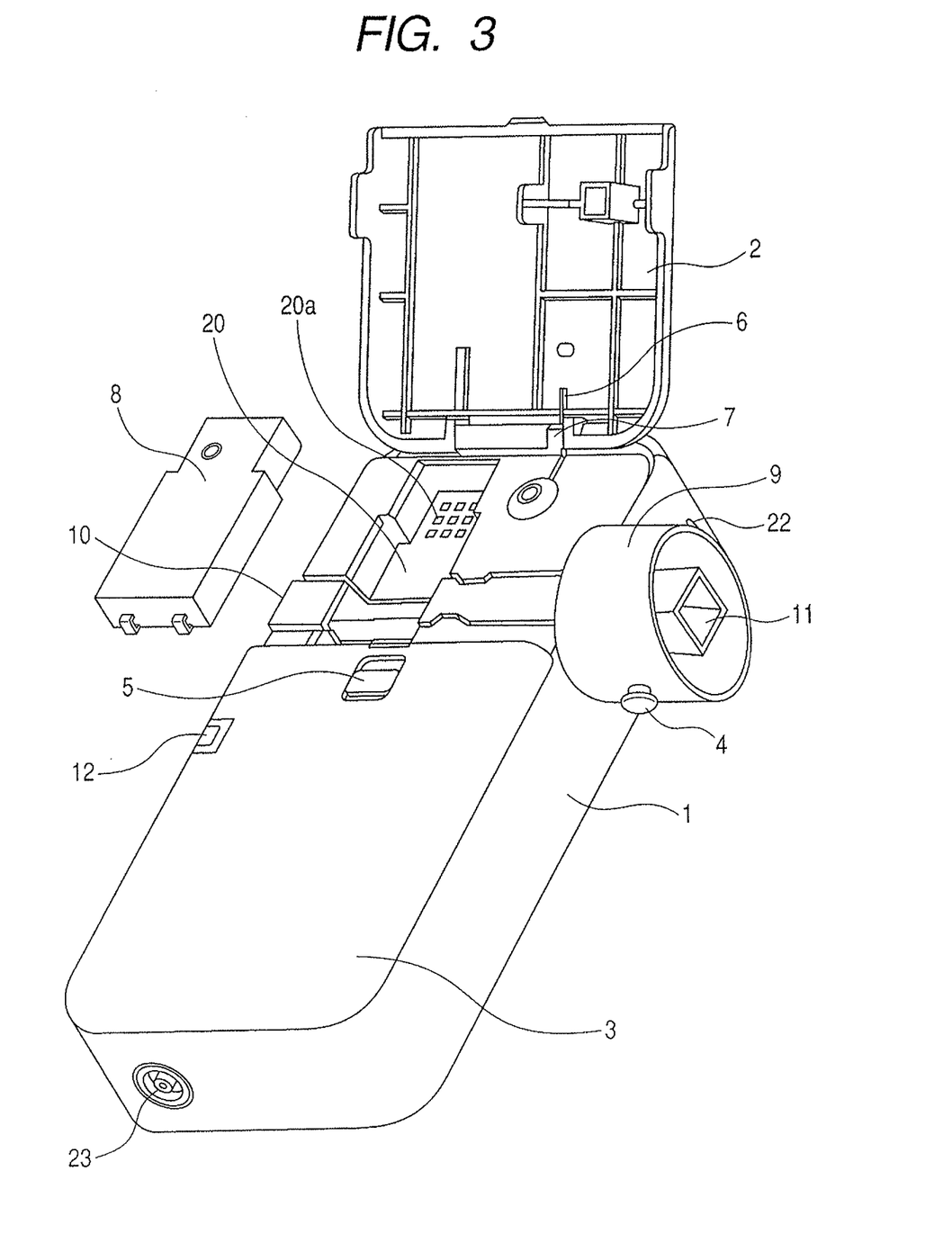
FIG. 3 is a view showing the appearance of the inhaling device according to an embodiment of the present invention at the time of opening the access cover.

FIG. 2 is a perspective view showing the appearance of the inhaling device 1 according to the embodiment. FIG. 3 is a perspective view showing the state in which an access cover 2 of the inhaling device 1 is opened, and a head tank unit 8 that is a drug ejection unit shown in FIG. 1 is taken out.

The access cover 2 opens with a hinge shaft 7 as a center of rotation by the force of an access cover return spring 6 which biases the access cover 2, when a lock lever 5 placed at a front cover 3 is slid downward. As illustrated in the drawings, in the embodiment, the head tank unit 8 is adapted to be attachable to and detachable from an attachment portion 20. A head portion ejecting a drug, a tank portion storing the drug solution before ejection, and a drug solution communication passage from the tank portion to the head portion integrally constitute the head tank unit 8.

A user holds a mouthpiece 9 in a mouth, breathes his or her breath and inhales the drug ejected from an inhaling port 11 continuing from the inhaling passage. The mouthpiece 9 and the inhaling port 11 constitute an inhaling port portion. A contact detection sensor 4 provided at the inhaling port portion outputs a signal indicating the inhalation intention of the user by detecting the contact state of the user with the inhaling port portion. Namely, the contact detection sensor 4 can output the signal by the user holding the mouthpiece 9 in the mouth, and therefore, the inhaling intention of the user can be read.

When the user holds the inhaling device body and contacts a hold detection sensor 12, the sensor outputs a signal indicating the inhalation intention of the user. A line 13 shows a grip area.

In the following description, the contact detection sensor 4 is a mouth switch, and the hold detection sensor 12 is a grip switch.

Figure 4:
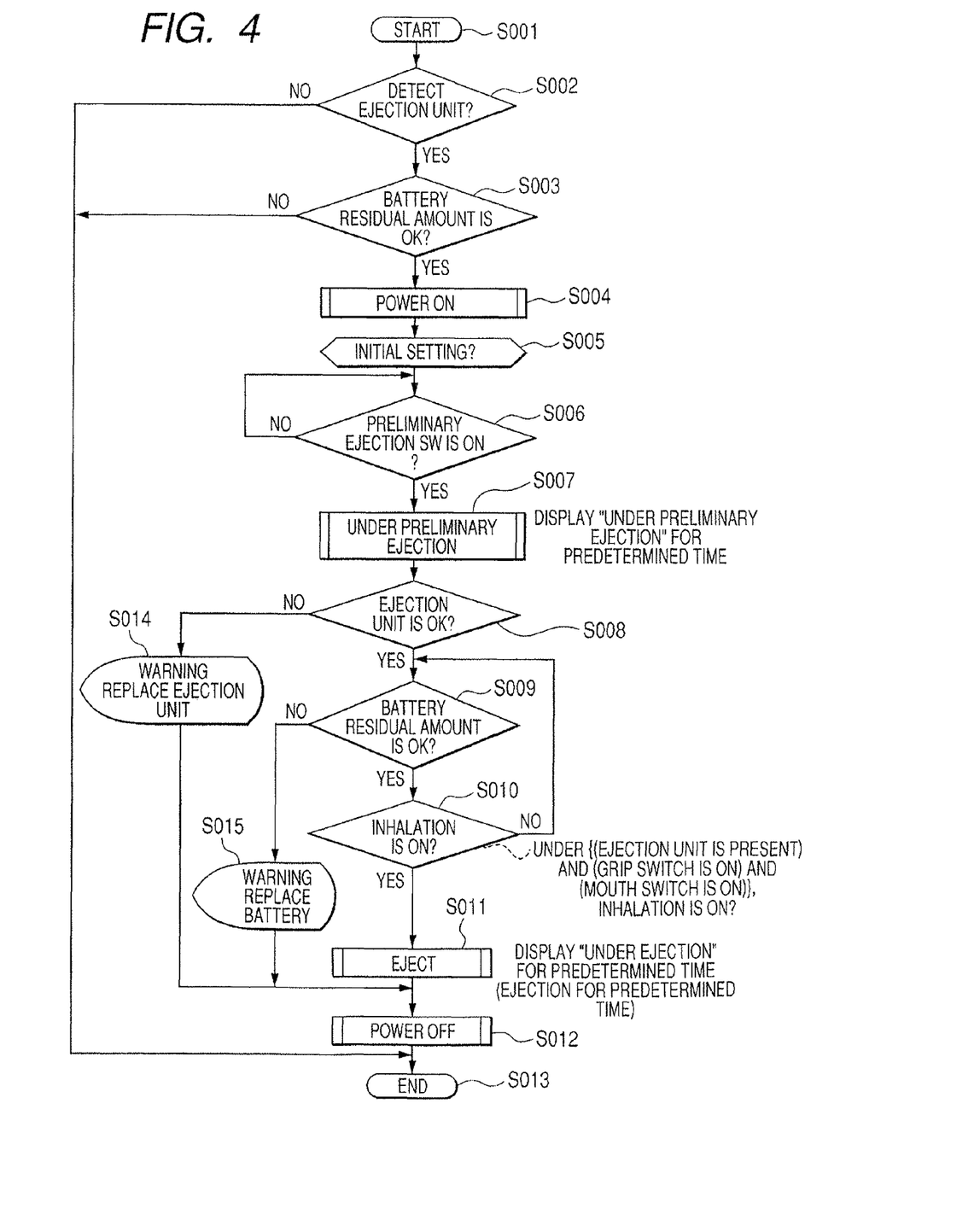
FIG. 4 is a flow chart showing an operation example of the inhaling device according to an embodiment of the present invention.
Figure 5:
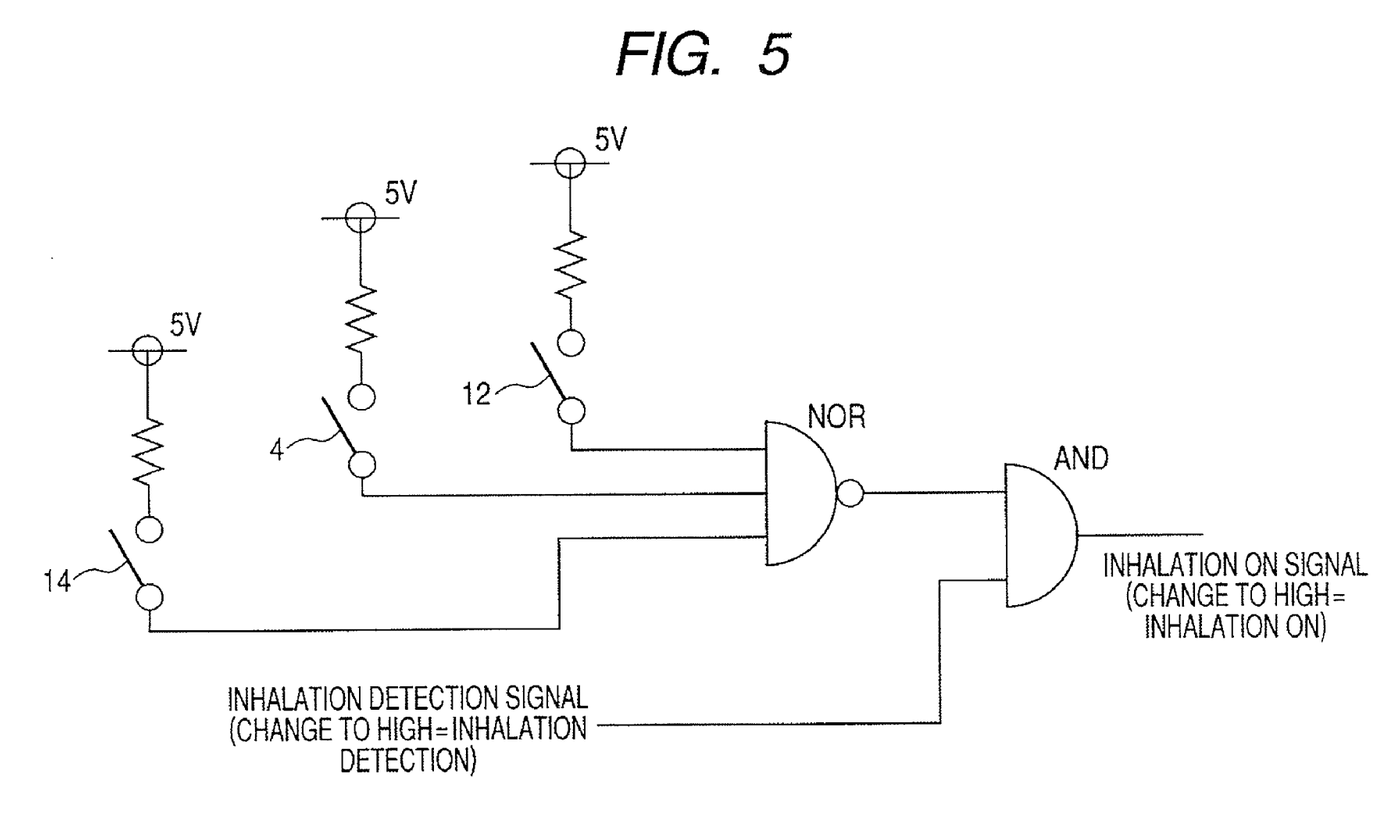
FIG. 5 is a circuit diagram for determining whether or not it makes an inhalation detection signal from an inhalation detecting portion (for example, a pressure sensor) effective, and makes an inhalation ON signal which is the source of an ejection signal effective, in an embodiment of the present invention.
Figure 6:
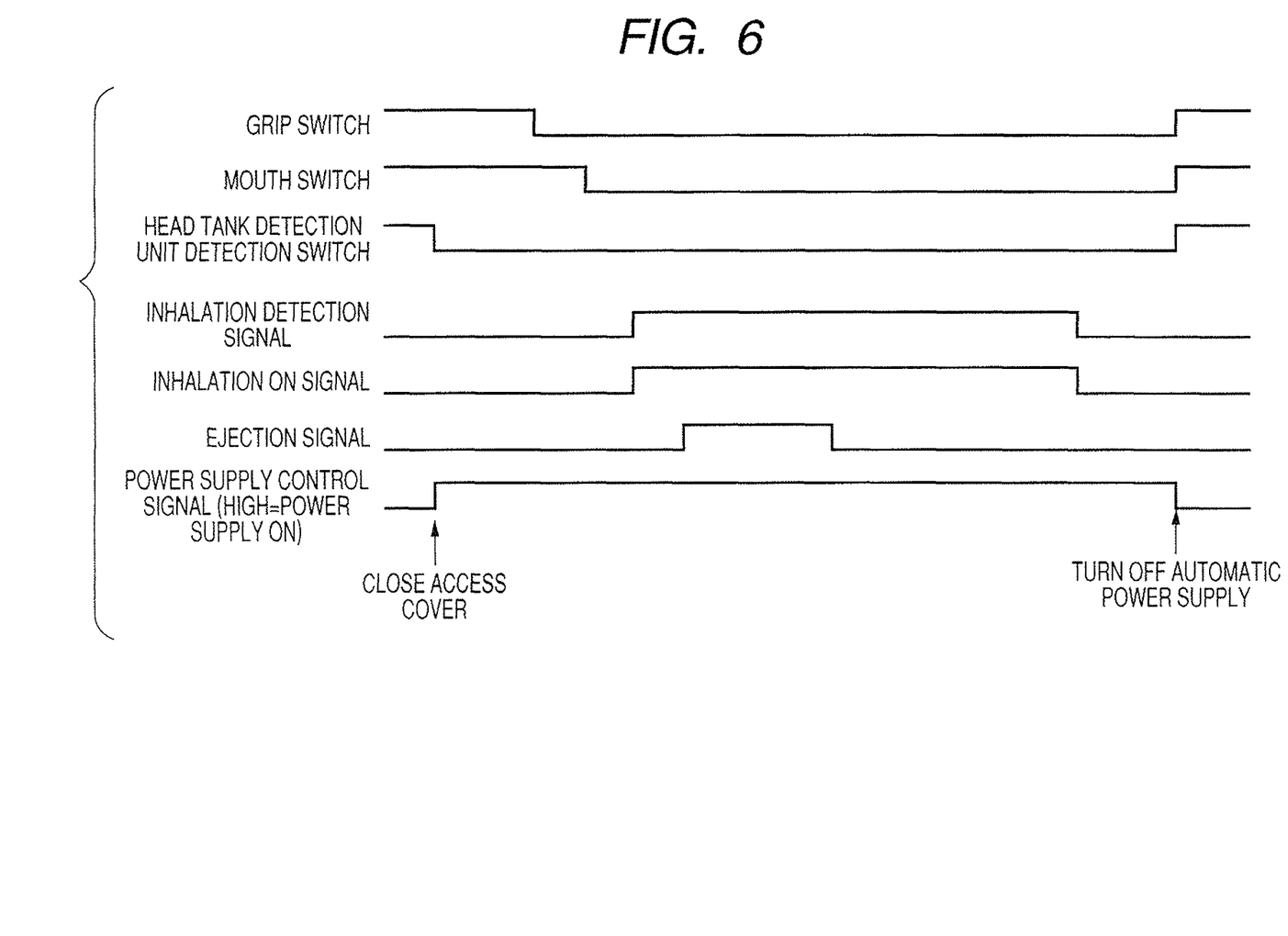
FIG. 6 is a timing chart for describing the circuit operation of FIG. 5, in an embodiment of the present invention.

Though not illustrated in FIGS. 2 and 3, a pressure sensor 30 for detecting inhalation of a user is provided in the inhaling passage formed by an air intake port 10 to the inhaling port 11. When the user performs inhalation, negative pressure occurs in the inhaling passage. When the negative pressure becomes a predetermined value or more, the pressure sensor 30 determines that the user performs inhalation, and outputs a signal showing the inhalation intention of the user (inhalation detection signal). A flowmeter may be provided in place of the pressure sensor, and when a predetermined flow is detected, it may be determined that the user performs inhalation. FIG. 4 is a flowchart showing the operation of the inhaling device of the embodiment. FIG. 5 is a diagram of a circuit which determines whether it makes the inhalation detection signal from the inhalation detection unit including the pressure sensor 30 and the like effective, and makes an inhalation ON signal which is the source of the ejection signal effective or not, and constitutes the determining portion in the present invention. A portion of FIG. 5 is included in the control unit shown in FIG. 1. FIG. 6 is a timing chart describing the circuit operation of FIG. 5 in the embodiment.

An operation of the embodiment as well as the configuration will be described with use of FIGS. 1, 2, 3, 4, 5 and 6, mainly with FIG. 4.

First, a power supply control signal (see FIG. 6) is ON by the user closing the access cover 2, and the device is in the use starting state (step S001. Hereinafter, described as S001 by omitting step). After start of use, presence or absence of the head tank unit 8 is checked (S002), and if the head tank unit 8 is absent, the power supply ON is not displayed and the flow directly ends (S013). The mounting detection portion of the head tank unit 8 is adapted to be able to detect with a head tank unit detection switch 14 shown in FIGS. 1 and 5. When the switch is ON, the mounting detection portion determines that the head tank unit is present, and outputs a signal indicating mounting to a mounting portion 20. When the switch is OFF, the head tank unit is absent. For example, when the head tank unit 8 performs ejection by the method of using a heater, the mounting detection unit of whether the head tank unit 8 is present in the mounting portion 20 or not can be realized by measuring the resistance value of the heater which is the ejection energy generating unit. However, in the present invention, the ejection actuator is not especially limited, and an electrothermal converter, a piezoelectric element and the like may be used as the ejection actuator. When the head tank unit 8 is mounted to the mounting portion 20, its electric connecting portion is connected to an electric contact point 20a of the mounting portion 20, and the head tank unit 8 receives electric power and various electric control signals from the battery and the control circuit on the apparatus body 1 side. The drug ejection device is typically the device adapted so as to be portably owned by a user.

When the head tank unit 8 is present, the battery residual amount detection unit checks the residual amount of the battery (S003), and when the inhalation operation is determined to be impossible, it does not make the display of power supply ON, and directly terminates the flow (S013). In this case, the display unit may make display which encourages replacement and charge of the battery. When the battery residual amount is determined to be enough to allow execution of at least one preliminary ejection and one inhalation operation, power supply ON is displayed (S004), and the initial setting (S005) is performed. Here, power ON may be displayed with an LED 22 or the like. The power supply is adapted to be chargeable through a charging port 23.

In this embodiment, the user needs to obtain a sense of security by the user visually confirming that the drug can be ejected without fail after completion of the initial setting (S005). Therefore, the user performs the preliminary ejection operation at least once. Accordingly, in an operation step (S006) of the preliminary ejection switch, the user presses the preliminary ejection switch shown in FIG. 1 while looking into the air intake port 10, and confirms the ejection operation of the inhaling device before inhalation. In the preliminary ejection, only the confirmation of the liquid being ejected normally is required, and therefore, a smaller amount of liquid than the amount of inhaled liquid can be ejected.

The preliminary ejection is started manually as above, and while the preliminary ejection is performed for a predetermined time, the display notifying the user that the device is under preliminary ejection is performed (S007). Thereafter, the ejection detection unit which is the preparation unit shown in FIG. 1 detects the drug solution preliminarily ejected (S008). As the detection unit of ejection, the unit detecting reflection light, refracted light, transmission light and scattered light by the ejected drug atmosphere, or the optical unit using laser are cited. Alternatively, the method for detecting the temperature change due to drug ejection by using infrared ray, and the method of using the humidity sensor detecting the capacity under the drug atmosphere and impedance change are cited.

When ejection cannot be detected here, the ejection unit 8 is determined to be NG (ejection failure). The flow goes to step (S014), and "Replace the ejection unit" is displayed for a fixed time. This notifies the user of an ejection failure, and turns the power off (S012). When the ejection can be detected, the flow goes to step (S009), and the battery residual amount is checked. Here, it is determined whether the battery residual amount allows execution of at least one inhaling operation. When it is NO, "Replace the battery" is displayed as warning for a fixed time (S015), and the flow goes to the POWER OFF operation (S012).

When the battery residual amount allows execution of at least one inhalation operation, and the determination is YES, the following operation is performed. It is determined whether {(the ejection unit 8 is present) and (grip switch 12 is on) and (mouth switch 4 is on)}, and further, inhalation is ON. The grip switch 12 is formed inside the line 13 indicating the grip area, and detects whether the user grips the inhaling device 1 or not. The mouth switch 4 is disposed near the inhaling port portion 11 of the mouth piece 9, and detects whether the user holds in the mouth the portion around the inhaling port portion 11. With respect to whether inhalation is performed to a predetermined extent or not, inhalation start is determined by detecting predetermined negative pressure by the inhalation operation of the user by using the pressure sensor (inhalation detection unit) 30 shown in FIG. 1.

When it is determined to be YES here, in the state of {(the ejection unit 8 is present) and (the grip switch 12 is on) and (mouth switch 4 is on)}, an inhalation detection signal is determined and the inhalation ON signal is output. This generates an inhalation detection signal by using the pressure sensor of FIG. 1, generates the ejection signal shown in FIG. 6 is from the inhalation ON signal shown in FIGS. 5 and 6, and generates the ejection signal for a predetermined time. In this way, when inhalation start is YES, the flow goes to step (S011), and when it is NO, the flow returns to step (S009). In step (S011), while the ejection signal is High (see FIG. 6), a drug solution is ejected for inhalation and "under ejection" is displayed for a predetermined time. When the predetermined ejection and inhalation are finished thereafter, the operation of POWER OFF (S102) is performed, and the flow ends (S013).

While the grip switch 12 and the mouth switch 4 are both on, and the pressure sensor detects predetermined negative pressure, ejection can be made. However, after a predetermined time elapses after the start of ejection, ejection of the liquid from the ejection head can be stopped regardless of the output signal. Namely, after the predetermined ejection amount is ejected, ejection can stop automatically. Thereby, the user can reliably inhale a desired amount of liquid.

The above described description shows the configuration which enables inhalation when detecting the signals indicating inhalation intention of the user from all of the grip switch, the mouth switch and the pressure sensor. The mode is a desirable mode, but if the two of the above description are combined as necessary, the user is allowed to perform reliable inhalation. As the combination of the first and the second sensors, the following can be cited as examples. Namely, the pressure sensor 30 and the mouth sensor 4, the pressure sensor and the grip sensor 12, and the mouth sensor 4 and the grip sensor 12.

According to the embodiment, only when the user holds the inhaling device 1 by hand and holds the portion around the inhaling port 11 of the mouthpiece 9 in the mouth, inhalation detection by the pressure sensor and the like which detect inhalation of the user effectively works. Therefore, even if the pressure sensor erroneously detects negative pressure by wind and the like, ejection is not performed unless the user is actually in the posture of inhalation, and an erroneous operation of the inhalation detection can be reliably prevented.

In the embodiment, it is confirmed that the head tank unit 8 having the tank portion storing a liquid is in the mounted state, and only when the preparation completion state is confirmed by the ejection detection unit preparing the state enabling ejection, ejection is enabled. Thereby, the user can inhale the liquid more reliably.

The present invention is characterized in that two or more sensors for detecting actions of the user relating to inhalation are provided, and ejection of a liquid from an ejection head, that is, driving of the head can be performed when both of these sensors output signals indicating inhalation intension of the user. However, immediately after all the sensors output the signals, the ejection must not be always started.

The ejection start timing is not limited at all. However, in order to allow the user to effectively inhale a drug, preferable ejection start timing will be described below.

In the case where a pressure sensor or a flowmeter is used in the inhaling passage as one sensor of the present invention, when all the sensors output the signals, it is preferable to immediately start ejection. This is because the pressure sensor or the flowmeter detects the actual inhalation action of the user. This is the embodiment as described above.

On the other hand, in the case where a pressure sensor or a flowmeter is not used as the sensor of the present invention, for example, only a grip switch 12 and a mouth switch 4 are used as the sensor of the present invention, a press button for outputting an ejection start signal may be provided for the start of ejection. So-called manual mode may be employed. When the press button is pressed in a state that all the sensors output signals, ejection starts. On the other hand, when the press button is pressed in a state that any one of the sensors does not output signal, ejection does not start. In this case, the device may have a structure, in which the grip switch is formed as a two-staged switch, such that after the user holds the body of the device, the user further presses the grip switch, whereby the ejection starts.

Figure 7:
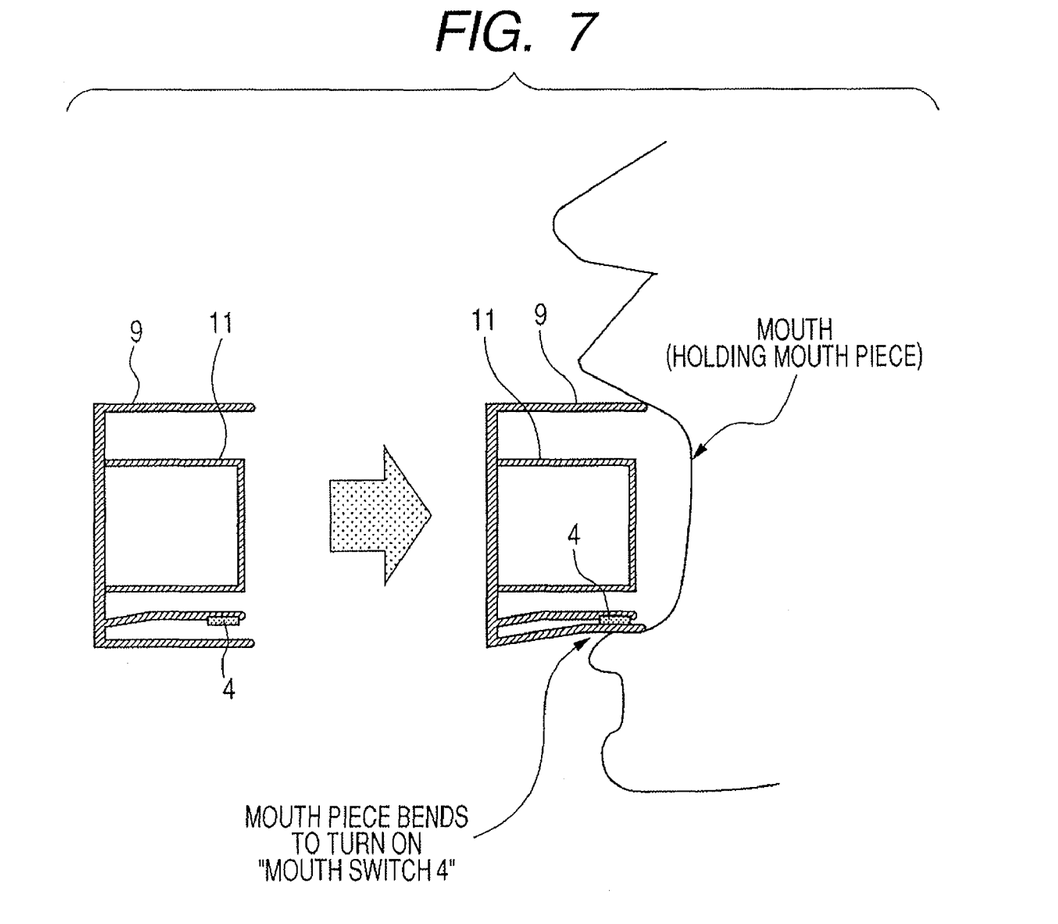
FIG. 7 is a schematic view for describing an operation example of a switch 4.

Here, the various forms of the mouth switch 4 will be described. FIG. 7 is a sectional view illustrating the operation of one example of the mouth switch 4. When the user holds the mouthpiece 9 which is the peripheral portion of the inhaling port 11 in the mouth, the mouthpiece 9 bends, whereby the switch 4 is turned on to start the operation flow as described above.

As the form of the contact detection, the following forms can be adopted.

A detection unit which measures the human body resistance value when the mouth or the nose of a user contacts with the device is adapted. This is, for example, the unit which has two electrode terminals exposed at the portion shown in FIG. 7, and measures the human body resistance value by contact of the oral cavity with them. The unit determines that the human body contacts the device when measuring the human body resistance value.

A detection unit which converts the distortion change of the capacitor electrode structure formed as the integrated structure with the inhaling port, which is caused by the force of the user when the user holds the mouthpiece 9 of the inhaling port portion in the mouth, into the change amount of the electrostatic capacity value, and measures the change amount can be adopted. This is the unit which has two electrode provided to be opposed to each other in the portion shown in FIG. 7, for example. The unit measures the change in the electrostatic capacity value due to a change of the space between the opposed electrodes by contact of the oral cavity as shown in FIG. 7. The detection unit determines that the human body contacts the device when measuring the change. In the switch 4 in FIG. 7, the switch portion is soft enough to contact the switch by being held in the mouth, but the detection unit can be realized by slightly increasing the rigidity of the switch so as to reduce the space. Further, the detection unit which converts the distortion change of the inductor structure formed as the integrated structure with the inhaling port, which is caused by the force of the user when the user holds the mouthpiece 9 in the mouth, into the change amount of the inductance and measures the change amount can be adopted. This is the unit which has the coil provided, for example, in the portion of the switch 4 shown in FIG. 7, and measures the change in inductance due to change of the coil by the oral cavity contacting with the coil as shown in FIG. 7. The detection unit determines that the human body contacts with the detection unit when measuring the change. Further, a contact detection unit which has conductive members provided in a plurality of portions of the inhaling port 11 is adapted. The contact detection unit measures the change amount of any one of inductance, capacitance, and impedance among the plurality of conductive members formed as the integrated structure with the inhaling port. In this case, the contact detection unit measures the change amount from the distortion change of the structure caused by the force of the user when the user holds the mouthpiece 9 in the mouth, and detects contact.

Further, the contact detection unit can be also adapted to determine contact and non-contact by detecting the biological reaction in the liquid ejecting direction of the inhaling port 11 with at least one of the temperature and action.

The contact detection unit can be adapted to determine contact and non-contact by detecting the structure of the inside of the oral cavity of the user in the liquid ejecting direction of the inhaling port 11, or the distance from the oral cavity. The detection unit of the structure or the distance emits sonic waves into the oral cavity from the area near the inhaling port, for example, and measures the reflection to determine contact and non-contact. Accordingly, in this configuration, a sonic wave emitting portion and a sonic wave detection portion are provided in the peripheral portion of the inhaling port 11. Alternatively, the contact detection unit may be adapted to determine contact and non-contact by emitting light or electric wave into an oral cavity from the area near the inhaling port, and measuring the reflection.

The present invention is not limited to the above embodiments and various changes and modifications can be made within the spirit and scope of the present invention. Therefore to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application-Open No. 2006-113703, filed Apr. 17, 2006, which is hereby incorporated by reference herein in its entirety.

What is claimed is:

1. A liquid ejection device comprising:
an inhaling port;
an ejection head for ejecting a liquid to be inhaled by a user through the inhaling port;
a first sensor having at least one of a pressure sensor and a flow meter, for outputting a first signal responsive to detection of a first phenomenon by the first sensor;
a second sensor for detecting an action of the user relating to inhalation and for outputting a second signal responsive to detection of the action, the second sensor being different from the first sensor; and
a determining portion for determining an operation of ejecting the liquid of the ejection head in response to both the first signal and the second signal,
wherein the determining portion is constructed to respond to a first state, in which the second sensor outputs the second signal while the first sensor is outputting the first signal, and to respond to a second state, in which the first sensor outputs the first signal while the second sensor is outputting the second signal, and responds to each of those states by enabling ejection of the liquid from the ejection head.

2. The liquid ejection device according to claim 1, further comprising a third sensor for detecting still another action of the user relating to inhalation and for outputting a third signal, the third sensor being different from the first sensor and the second sensor, wherein the determining portion enables ejection of the liquid from the ejection head, in a state in which the second sensor outputs the second signal and the third sensor outputs the third signal, when the first sensor outputs the first signal.

3. The liquid ejection device according to claim 1, wherein the second sensor is any one of a contact detection sensor provided in the inhaling port for detecting contacting state of the user with the inhaling port, and a hold detection sensor provided in a liquid ejection device body for detecting holding state of the user of the liquid ejection device body.

4. The liquid ejection device according to claim 2, wherein the second sensor is a contact detection sensor provided in the inhaling port for detecting contacting state of the user with the inhaling port, and wherein the third sensor is a hold detection sensor provided in a liquid ejection device body for detecting holding state of the user of the liquid ejection device body.

5. The liquid ejection device according to claim 1, wherein the determining portion drives the ejection head so as to eject the liquid from the ejection head in response to a signal to start preliminary ejection regardless of the first signal and the second signal.

6. The liquid ejection device according to claim 1, further comprising:
   a mounting portion for attachably and detachably mounting a head tank unit which is a combination of an ejection head portion, a tank portion for storing a liquid, and a liquid communication passage from the tank portion to the head portion; and
   a mounting detection portion for detecting that the head tank unit is mounted on the mounting portion,
   wherein the determining portion enables ejection of the liquid from the ejection head when the mounting detection portion outputs a signal indicating that the head tank unit is mounted on the mounting portion.

7. The liquid ejection device according to claim 1, wherein the determining portion stops ejection of the liquid from the ejection head regardless of the first signal and the second signal after a predetermined time elapses from the start of ejection of the liquid from the ejection head.

* * * * *